(12) United States Patent
Hammerschmidt et al.

(10) Patent No.: US 9,956,534 B2
(45) Date of Patent: May 1, 2018

(54) METHOD AND DEVICE FOR SUSPENDING CELLS

(71) Applicant: Miltenyi Biotec GmbH, Bergisch Gladbach (DE)

(72) Inventors: Dominik Hammerschmidt, Lindlar (DE); Sven Ignatius, Bergisch Gladbach (DE); Martin Buscher, Bergische Gladbach (DE); Ralf-Peter Peters, Bergisch Gladbach (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 0 days. days.

(21) Appl. No.: 15/676,048

(22) Filed: Aug. 14, 2017

(65) Prior Publication Data

US 2017/0361289 A1 Dec. 21, 2017

Related U.S. Application Data

(63) Continuation-in-part of application No. 14/705,037, filed on May 6, 2015.

(30) Foreign Application Priority Data

May 17, 2014 (EP) .................................. 14168756

(51) Int. Cl.
| | |
|---|---|
| *B01F 13/08* | (2006.01) |
| *B01F 11/00* | (2006.01) |
| *B01F 15/02* | (2006.01) |
| *B01F 15/00* | (2006.01) |
| *C12M 1/06* | (2006.01) |
| *G01N 1/38* | (2006.01) |
| *G01N 35/10* | (2006.01) |

(52) U.S. Cl.
CPC ...... *B01F 13/0854* (2013.01); *B01F 11/0082* (2013.01); *B01F 11/0091* (2013.01); *B01F 13/08* (2013.01); *B01F 13/0827* (2013.01); *B01F 15/00032* (2013.01); *B01F 15/0203* (2013.01); *C12M 27/02* (2013.01); *G01N 1/38* (2013.01); *B01F 2215/0037* (2013.01); *G01N 2001/386* (2013.01); *G01N 2035/1058* (2013.01)

(58) Field of Classification Search
CPC ............................. B01F 13/08; B01F 13/0854
USPC .................................................. 366/273–274
See application file for complete search history.

(56) References Cited

U.S. PATENT DOCUMENTS

| | | | | | |
|---|---|---|---|---|---|
| 2,932,493 | A | * | 4/1960 | Jacobs ................ | A47J 43/0465 219/433 |
| 3,572,651 | A | * | 3/1971 | Harker .................... | B01F 11/04 366/185 |
| 3,744,764 | A | * | 7/1973 | Sedam ................ | B01F 13/0827 222/137 |
| 3,854,704 | A | * | 12/1974 | Balas ...................... | B01F 11/04 366/102 |
| 3,863,903 | A | * | 2/1975 | Brehmer ............. | B01F 13/0827 366/274 |
| 3,888,466 | A | * | 6/1975 | Sedam ................ | B01F 13/0827 222/226 |

(Continued)

*Primary Examiner* — Abbas Rashid
(74) *Attorney, Agent, or Firm* — Jacquelin K. Spong

(57) ABSTRACT

The invention is related to a device for suspending particles in a fluid, wherein the mixing device includes a first magnet (1) rotating around a longitudinal axis (2), a mixing rod (4) attached to a mount (6), the mount including a second magnet (3), wherein the mount (6) moves in a substantially orthogonal motion to the longitudinal axis of the mixing rod (4) by the interaction of the rotating first magnet with the second magnet (3).

14 Claims, 6 Drawing Sheets

(56) References Cited

U.S. PATENT DOCUMENTS

| | | | | |
|---|---|---|---|---|
| 3,900,186 | A * | 8/1975 | Balas | B01F 11/04 366/168.1 |
| 4,046,515 | A * | 9/1977 | de Leeuw | B01F 11/008 366/117 |
| 4,204,774 | A * | 5/1980 | de Bruyne | B01F 7/30 366/102 |
| 4,289,854 | A * | 9/1981 | Tolbert | B01F 7/0005 366/273 |
| 4,382,685 | A * | 5/1983 | Pearson | B01F 7/30 366/241 |
| 4,465,377 | A * | 8/1984 | de Bruyne | B01F 13/0818 366/273 |
| 4,649,118 | A * | 3/1987 | Anderson | B01F 11/04 366/255 |
| 7,249,880 | B2 * | 7/2007 | Zambaux | B01F 7/1695 366/277 |
| 2004/0253716 | A1 * | 12/2004 | Jaeger | C12M 23/02 435/299.2 |
| 2008/0078257 | A1 * | 4/2008 | Daniel | B01F 11/0077 73/864.01 |
| 2010/0246317 | A1 * | 9/2010 | Wilson | A01J 5/0132 366/142 |
| 2012/0127821 | A1 * | 5/2012 | Dunfee | B01F 11/0014 366/142 |
| 2014/0133265 | A1 * | 5/2014 | Francis | B01F 13/0863 366/273 |
| 2015/0328605 | A1 * | 11/2015 | Hammerschmidt | B01F 13/08 366/273 |

* cited by examiner

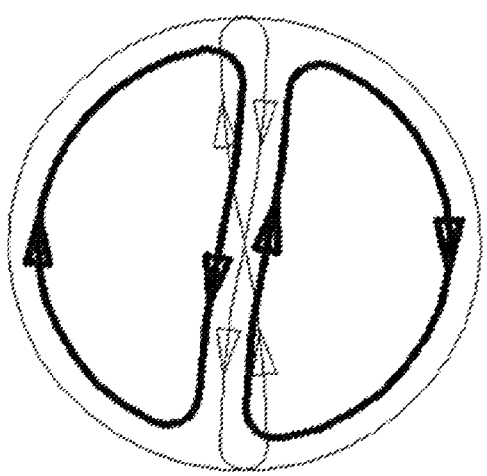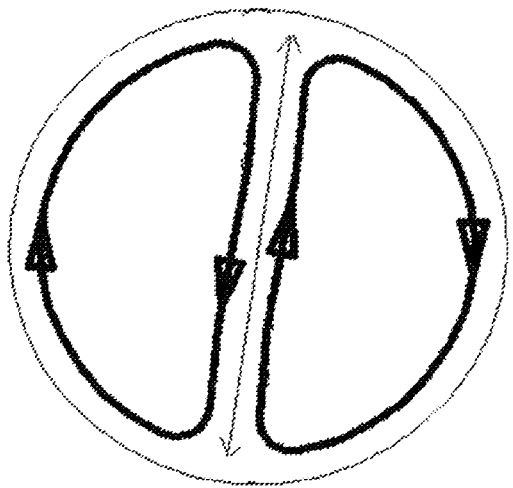
Fig. 6a
Fig. 6b

US 9,956,534 B2

METHOD AND DEVICE FOR SUSPENDING CELLS

CROSS REFERENCE TO RELATED APPLICATIONS

This U.S. Patent Application is a Continuation-In-Part, claiming priority to U.S. patent application Ser. No. 14/705,037, which in turn claims priority to European Patent Application Serial No. 14168756.6, filed May 17, 2014. Each of these applications are incorporated by reference in their entirety.

STATEMENT REGARDING FEDERALLY SPONSORED RESEARCH

Not applicable.

STATEMENT REGARDING MICROFICHE APPENDIX

Not applicable.

BACKGROUND

This invention relates to a method and a device for suspending particles in a fluid, especially for suspending living cells in a small volume of fluid.

Biological samples like cells need to be suspended in a liquid for culturing or analyzing purposes. Such suspensions are stable for a short time until the sample starts sedimentation which makes remixing necessary. Mixing suspensions of biological samples is a long known technique for which various devices are commercially available. Design and function of the mixing devices depend on the nature and volume of the sample to be mixed, the size and form of the mixing vessel and subsequent processing steps of the sample.

Besides mixing a suspension by a stirrer coupled to an electric motor, magnetic cell stirrers are in common use. To provide larger volumes of suspensions, EP53869, U.S. Pat. No. 3,854,704 and U.S. Pat. No. 3,572,651 disclose a magnetic cell stirrer wherein the suspension is mixed by a rotating magnet placed in the mixing vessel via a flexible shaft. The magnet inside of the vessel is forced into rotational movement by a magnet outside of the vessel which in turn is rotated by a conventional magnetic stirring apparatus. The flexible shaft is attached to the mixing vessel and can not be removed or inserted into the vessel.

U.S. Pat. No. 3,780,992 discloses a vibrating pipette, wherein a mechanical oscillator is attached to the pipette as a mixing rod.

U.S. Pat. No. 4,204,774 describes a magnetic cell stirrer wherein the suspension is mixed by a rotating stirring rod. The rod is rotated in a circular path in the mixing vessel by an eccentric means and a synchronous motor. The magnetic cell stirrer is firmly attached to the mixing vessel and can not be removed or inserted into the vessel.

Biological samples for testing or analyzing purposes are usually provided in small volumes ranging from less than 10 µl to 5 ml. For example, commonly used microplates provide up to 1024 wells having a volume less than one milliliter. Mixing of such small volumes by mere stirring is difficult due to capillary forces and a low surface to volume ratio of the vessel resulting in adhesion of the liquid to the vessel walls. Mixing by stirring generates a single stream of liquid moving in a circle adjacent to the vessel wall having low turbulence and accordingly a low mixing efficiency.

In this respect, US2008/0078257 discloses a mixing process, wherein a magnetic mixing rod is moved by a second magnet rotating around the mixing rod.

Suspensions in microplate wells are therefore usually mixed by shaking or vibrating the whole microplate i.e. all wells simultaneously. Shaking cell suspensions in a microplate might result in cell loss since cells can adhere to walls of a well above the surface of the liquid It would be beneficial to provide small volume suspensions of biological samples without stirring the fluid in circles and/or the need to shake/vibrate other vessels. It would furthermore be desirous to provide a device to generate such suspensions which can be implemented in analytical devices like a FACS machines for sample preparation upstream of the cell analysis device.

Surprisingly, it was found that particle suspensions, especially in small volume containers can be efficiently homogenized by a device wherein a magnetic mixing rod is moved in an oscillating manner by interaction with a rotating second magnet.

SUMMARY

Accordingly, the object of the invention is a mixing device comprising: a first magnet (1) rotating around a longitudinal axis (2); a mixing rod (4) attached to a mount (6), the mount including a second magnet (3), wherein the mount (6) moves in a substantially orthogonal motion to the longitudinal axis of the mixing rod (4) by the interaction of the rotating first magnet with the second magnet (3).

Another object of the invention is a process for mixing a biological sample like a cell suspension by providing the biological sample in a liquid into a mixing vessel, submerging a mixing rod (4) in the liquid and stirring the liquid by a first magnet (1) rotating around a longitudinal axis (2); a mixing rod (4) located inside a sleeve (10) attached to a mount (6), the mount including a second magnet (3), wherein the mount (6) moves in a substantially orthogonal motion to the longitudinal axis of the mixing rod (4) by the interaction of the rotating first magnet with the second magnet (3).

With the method and device of the invention, it is possible to suspend particles even in small volumes of fluid without loss of particles or fluid due to spilling or re-agglomeration.

Within the scope of the invention, the terms "mixing" or "suspending" are synonymous and are intended to mean generating a suspension of particles like cells in a fluid.

The method and device according to the invention is especially useful for suspending particles like a biological sample in a liquid or fluid by the movement of the mixing rod (4) in the biological sample. "Biological sample" can be any type of tissue or cells to be suspended in an appropriate fluid like cell nutrition buffer.

BRIEF DESCRIPTION OF THE DRAWINGS

FIGS. 6a and 6b show examples of movement of the mixing rod (4) (thin line) and resulting convection currents of fluids (bold line).

DETAILED DESCRIPTION

Figure 1:
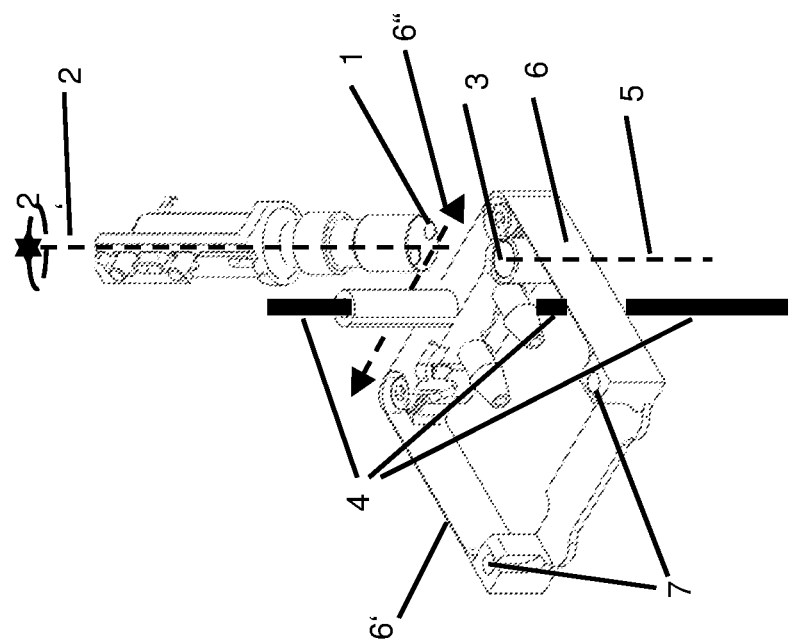
FIG. 1 shows the device with first magnet (1), first longitudinal axis (2, 2'), second magnet (3), mixing rod (4), mount (6, 6') and second axis (5)

The preferred movement of the mixing rod (4) through the fluid is substantially orthogonal or lateral in view of the longitudinal axis of the mixing rod. Such movement and the resulting currents in the liquid are depicted in FIG. 6 with arrows indicating the direction of movement. By moving the mixing rod (4) (thin lines) through the fluid, convection currents of fluid (bold lines) result with a common zone of turbulence. The currents flow with opposite direction and share at least one common zone of turbulence.

Essential for the mixing device according to the invention is the movement of the mixing rod (4) about the second axis (5). The term "substantially" means that the movement may deviate slightly from the lateral movement. For example, in FIG. 6a, the drawing shows in thin line a substantial lateral paths of movement of the mixing rod. It is preferred that the movement of the mixing rod (4) is lateral, i.e. orthogonal to the longitudinal axis of the mixing rod (4) as shown in FIG. 6b.

In the mixing device according to the invention, in quiescent state of the first magnet the longitudinal axis (2) of the first magnet may by substantially coaxial with a rotational axis of the second magnet (3).

The movement of the mixing rod originates from the rotation of the first magnet (1) around first axis (2). This rotational movement is transferred by magnetic interaction between the first magnet (1) and the second magnet (3) to the mount (6) and finally to the mixing rod (4). Magnetic interaction between the first magnet (1) and the second magnet (3) requires that the distance between the magnets is sufficiently small. Depending on the orientation of the poles of the first (1) and second (3) magnet, the interaction may generate attracting or opposing forces. In the present invention, first (1) and second (3) magnets are preferably oriented with the same pole facing each other (N-N or S-S). The rotational movement of first magnet (1) and the opposing forces between the magnets "pushes" second magnet (3) into motion.

First magnet (1) and the second magnet (3) are permanent magnets without any special requirements.

Figure 3:
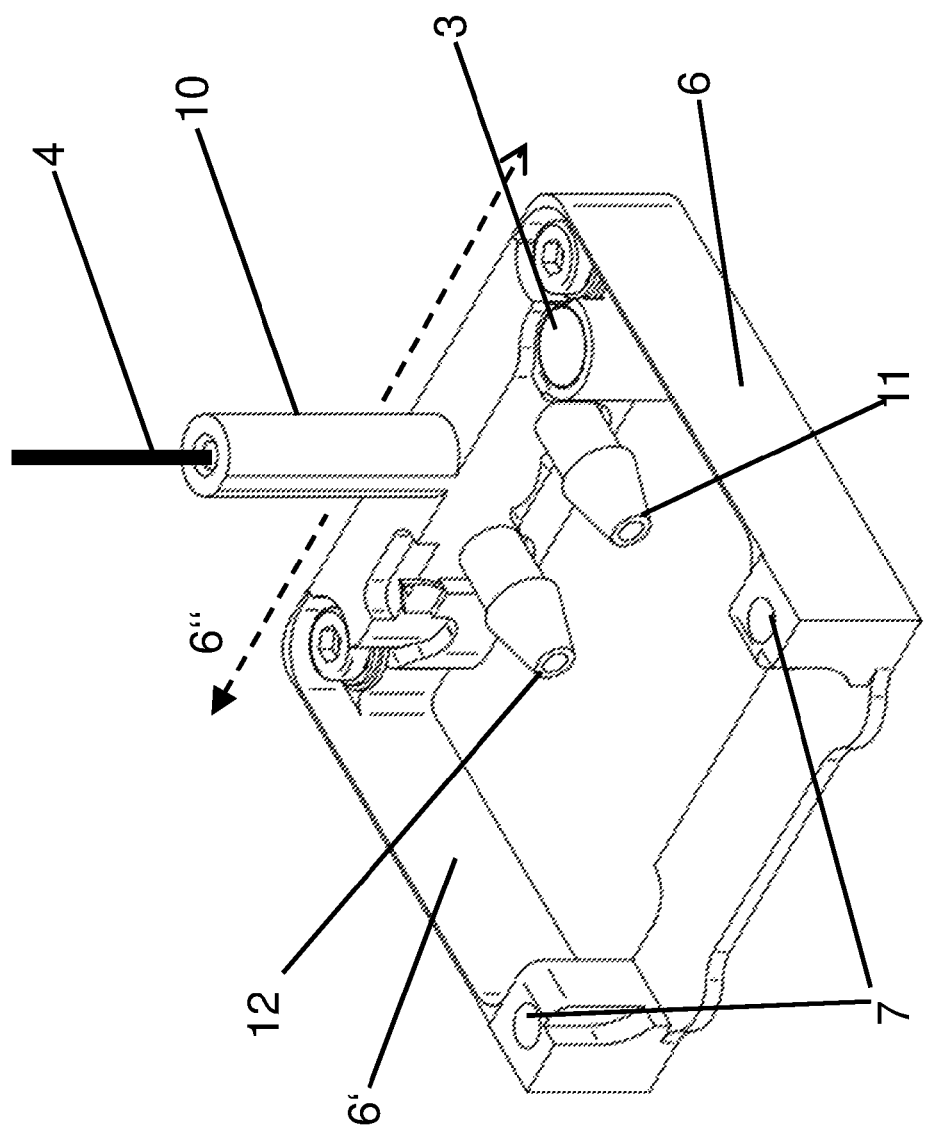
FIG. 3 shows second magnet (3) attached to the mount (6, 6') of mixing rod (4); hinged to joints (6 6'). The joints are fixed by through holes (7), thereby movement of the mount is limited as depicted by dashed line 6". Mixing rod (4) is guided by sleeve (10)

In FIGS. 1 and 3, the mixing rod (4) is guided by sleeve or guidance (10) which is attached to mount or hinge (6, 6'). The moving path of the mixing rod (4) is defined or restricted by the mount (6, 6') that allows movement of the second magnet (3) about a second axis (5). In a preferred embodiment of the invention, mount (6) is provided as holder with one or two sheet-like hinges which can only swing or vibrate joint (6) about the second axis (5). Accordingly, the mixing device may include a first magnet (1) rotating around a longitudinal axis (2), a mixing rod (4) attached to a mount (6), the mount including a second magnet (3), wherein the mount (6) moves in a substantially orthogonal motion to the longitudinal axis of the mixing rod (4) by the interaction of the rotating first magnet with the second magnet (3) wherein the orthogonal motion is defined by a plurality of joints disposed on at least two sides of the mount (6) and wherein the plurality of joints allows movement of the second magnet (3) only about a second axis (5) and orthogonal to the longitudinal axis.

In a preferred embodiment of the mixing device, mixing rod (4) is coupled to a mount (6) by a sleeve (10), wherein the sleeve allows movement of the mixing rod along its longitudinal axis. The orthogonal motion of the mixing rod may be accommodated by a plurality of joints disposed on at least two sides of the mount (6). This embodiment is shown in FIG. 3 and results in a substantial lateral movement of the mixing rod (4) along dashed line 6".

Figure 2:
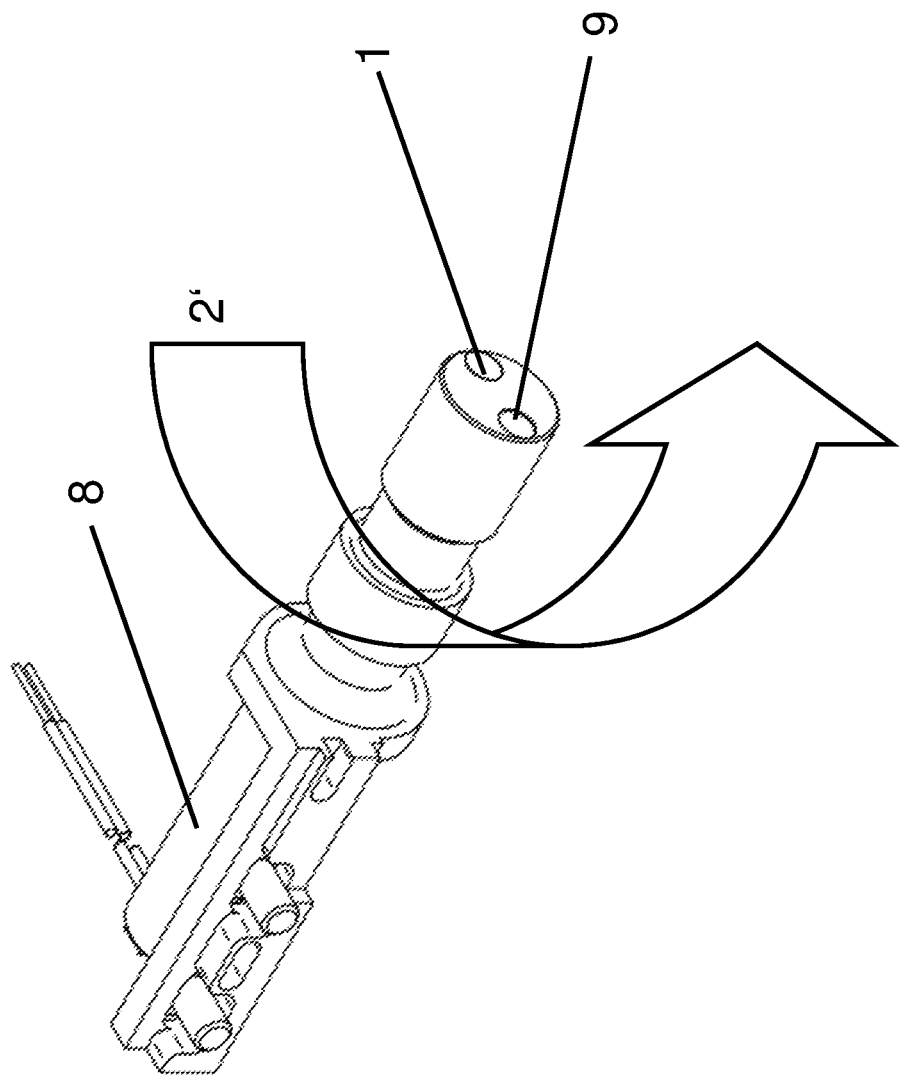
FIG. 2 shows the first magnet (1) mounted on electric motor (8) with counter weight (9) rotating around first longitudinal axis (2')

As shown in FIG. 2, rotation of the first magnet (1) is accomplished by an electric motor (8) which rotates around a first axis (2). The first magnet (1) may be fixed in line with the first axis (2) or in a preferred embodiment, asymmetric to the first axis (2) i.e. positioned with a distance of 1-5 mm to the first axis (2). In this embodiment, it is preferable that a counterweight (9) to the first magnet (1) is positioned at the same distance to the first axis (2) to prevent imbalance.

The mixing rod (4) is manufactured from a material like stainless steel or the like in contrast to flexible materials like polymers, rubber etc. The mixing rod (4) may be solid or provided as tube or cannula.

If provided as tube or cannula, the mixing rod (4) may be used for filling the mixing vessel with the particles and fluids to be mixed/suspended. In another variant of the invention, the particles (biological sample/cells) and/or the fluid are at least in part inserted or removed from the mixing vessel through a mixing rod (4) provided as tube. Particles and fluids may already be premixed before being provided into the mixing vessel. For this purpose, mixing rod (4) is optionally provided with appropriate connectors like the Luer-system for connection with tubing set.

Figure 4:
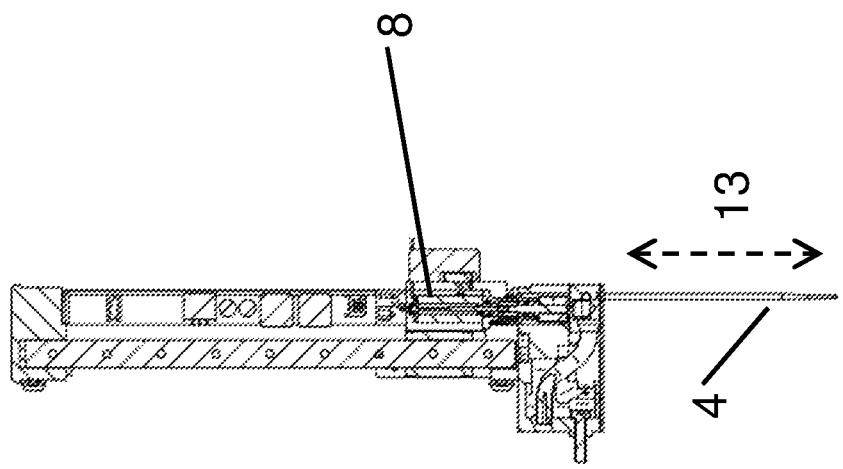
FIG. 4 side view of the mixing system with electric motor (8) and mixing rod (4)
Figure 5:
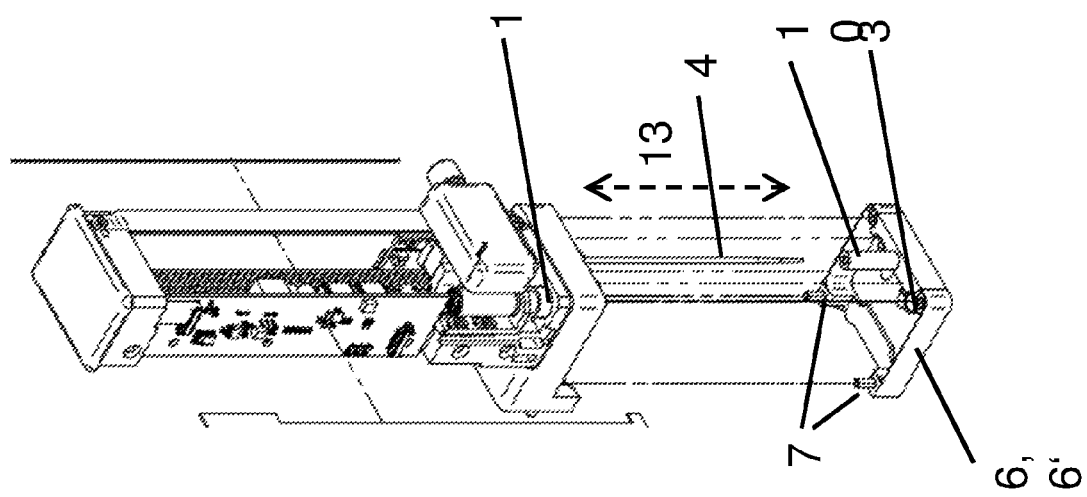
FIG. 5 front view of the mixing system with the hinged joints (6, 6') for the mixing rod (4) removed. Mixing rod (4) is guided by holder or sleeve (10)

In yet another embodiment of the invention, the mixing device is provided with at least one mixing vessel and the mixing rod can be inserted into and withdrawn from the mixing vessel. Inserting/withdrawing of the mixing rod from the vessel requires either moving the mixing vessel relative to a stationary mixing rod or moving the mixing rod relative to a stationary mixing vessel. This variant is shown in FIGS. 4 and 5, with the position of mixing rod (4) being adjustable relative to a (not shown) mixing vessel in direction of dashed line (13).

In a first variant of this embodiment of the invention, the mixing device is provided with at least one mixing vessel containing a liquid below the mount (6), such that the mixing rod (4) is submerged in the liquid so as to stir the liquid by the orthogonal motion. In this variant, the mixing device further comprises a driver 14 coupled to the motor 8, that stops and reverses the motion of the mixing rod (4), as shown in FIG. 2.

In a second variant of this embodiment of the invention, the mixing device is provided with at least one mixing vessel and the mixing rod (4) is inserted and removed from the mixing vessel by moving the mixing vessel in the direction along the longitudinal axis of the mixing rod (4).

As mixing vessels, the wells of commercially available microplates are preferred. Of course, the movement of the second magnet (3) and mixing rod (4) about the second axis (5) needs to be adjusted to the space available within the vessel. The mixing rod shall mix the liquid without touching the walls of the vessel throughout its movement.

The method of the invention is preferably performed in a mixing vessel wherein the ratio of the outer diameter of the mixing rod (4) and the maximum inner width of the mixing vessel is between about 0.1 and about 0.3. For example, the mixing rod (4) may have an outer diameter of 1.5 to 0.3 mm and may be utilized in mixing vessels with a maximum inner width of 1 to 10 mm.

The method and device of the invention can be used for mixing or suspending subsequently a plurality of different samples. It is another object of the invention to avoid contamination of a sample to be suspended by traces or drops of a different sample adhering to the mixing rod (4).

In further embodiments of the invention, the surface of the mixing rod is cleaned or stripped from adhering mixture by a cleaning pod or a cleaning liquid. For this purpose, the mount (6) may be provided with at least a cleaning pod that removes material from the mixing rod (4). The cleaning pod may be made from any material suitable for soaking up liquids like cotton or tissue paper.

Better cleaning of the mixing rod (4) can be achieved by using a cleaning liquid and washing the mixing rod (4). In this embodiment of the invention, the mount (6) is provided with at least one orifice (11, 12) which allows the introduction of a liquid into the sleeve (10). The mixing rod (4) is then guided through a reservoir of the cleaning liquid or through a stream of cleaning liquid, thereby assuring that the mixing rod (4) is only in contact with fresh, uncontaminated cleaning liquid.

FIG. 3 shows this embodiment of the invention, where joint or hinge (6, 6') is provided with sleeve or guidance (10) for the mixing rod (4) which can be flushed with cleaning liquid provided and removed through orifices (11) and (12).

The method and device according to the invention is especially useful for sample preparation in automated processing or analyzing of biological samples. Usually, such processing requires a homogenous suspension of the sample in a fluid. At best, the homogenous sample is suspended in the fluid shortly before processing.

Accordingly, another object of the invention is a process for providing a suspension, comprising: placing particles like a biological sample and a fluid in a mixing vessel; placing the mixing rod (4) of the mixing device as described in the mixing vessel and suspending the particles in the liquid/fluid. The mixing rod may thereby mix the biological sample.

The process of the invention can be utilized within high-throughput automates or robots for analyzing a plurality of biological samples. Therefore, multi-well microplates are preferably used as a mixing vessel in the process of the invention and the mixing rod (4) is inserted in each well/mixing vessel for mixing and withdrawn after suspending/mixing is completed.

The device and method of the invention can be used for parallel processing of a plurality of samples. For example, suspending of a plurality of biological samples on multi-well microplates may be performed in parallel by 2 to 6 devices of the invention. For this purpose, the mixing device may comprise an additional 1 to 6 mixing rods (4) and mounts (10) which are driven in parallel.

On the other hand, the mixing device may be used for larger volumes by using one mount (6) which includes a plurality of mixing rods (4).

The mixing device of the invention can be used for any automated processing or automated analyzing of biological samples in suspension or solution, especially ELIZA or FACS systems.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A mixing device comprising:
   a first magnet (1) rotating around a longitudinal axis (2);
   a mixing rod (4) attached to a mount (6), the mount including a second magnet (3), wherein the mount (6) moves in a substantially orthogonal motion to the longitudinal axis (2) of the mixing rod (4) by an interaction of the rotating first magnet with the second magnet (3) wherein the orthogonal motion is accommodated by a plurality of joints disposed on at least two sides of the mount (6) and wherein the plurality of joints allows movement of the second magnet (3) only about a second axis which is orthogonal to the longitudinal axis (2).

2. The mixing device according to claim 1, wherein the longitudinal axis (2) of the first magnet is substantially coaxial with a rotational axis of the second magnet (3).

3. The mixing device according to claim 1, characterized in that the mixing rod is a tube.

4. The mixing device according to claim 1, characterized in that the mixing rod (4) is coupled to the mount (6) by a sleeve (10), wherein the sleeve allows movement of the mixing rod along its longitudinal axis.

5. The mixing device according to claim 1, characterized in that the mount (6) is provided with at least one orifice (11, 12) which allows introduction of a liquid into a sleeve (10).

6. The mixing device according to claim 1, characterized in that the mount (6) is provided with at least a cleaning pod that removes material from the mixing rod.

7. The mixing device according to claim 1, characterized in that at least one mixing vessel containing a liquid is provided below the mount (6), such that the mixing rod is submerged in the liquid so as to stir the liquid by the orthogonal motion.

8. The mixing device according to claim 1, characterized in that at least one mixing vessel is provided and the mixing rod (4) is inserted and removed from the mixing vessel by moving the mixing vessel in a direction along the longitudinal axis of the mixing rod (4).

9. The mixing device according to claim 1, wherein the mixing rod does not touch walls of a mixing vessel throughout its movement.

10. The mixing device according to claim 7, wherein the outer diameter of the mixing rod (4) is between about 0.1 and 0.3 of a diameter of the vessel.

11. The mixing device according to claim 1, further comprising an additional 1 to 6 mixing rods (4) and mounts (10) which are driven in parallel.

12. The mixing device according to claim 1, wherein the mount (6) includes a plurality of mixing rods (4).

13. The mixing device according to claim 1, further comprising a driver that stops and reverses motion of the mixing rod.

14. The mixing device according to claim 1, wherein the mixing rod (4) mixes a biological sample.

* * * * *